(12) United States Patent
Peli et al.

(10) Patent No.: US 11,270,451 B2
(45) Date of Patent: Mar. 8, 2022

(54) MOTION PARALLAX IN OBJECT RECOGNITION

(71) Applicant: The Schepens Eye Research Institute, Inc., Boston, MA (US)

(72) Inventors: Eliezer Peli, Boston, MA (US); JaeHyun Jung, Winchester, MA (US); Cheng Qiu, Medford, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 92 days.

(21) Appl. No.: 16/498,027

(22) PCT Filed: Mar. 16, 2018

(86) PCT No.: PCT/US2018/022916
§ 371 (c)(1),
(2) Date: Sep. 26, 2019

(87) PCT Pub. No.: WO2018/183000
PCT Pub. Date: Oct. 4, 2018

(65) Prior Publication Data
US 2020/0034980 A1    Jan. 30, 2020

Related U.S. Application Data

(60) Provisional application No. 62/479,160, filed on Mar. 30, 2017.

(51) Int. Cl.
*G06T 7/593* (2017.01)
*H04N 13/204* (2018.01)
(Continued)

(52) U.S. Cl.
CPC .......... *G06T 7/593* (2017.01); *G06K 9/00912* (2013.01); *G06K 9/3241* (2013.01);
(Continued)

(58) Field of Classification Search
CPC ................ G06T 7/593; G06T 2200/04; G06T 2207/10012; G06T 2207/10028;
(Continued)

(56) References Cited

U.S. PATENT DOCUMENTS 5,060,062 A   10/1991   Dotson
5,760,950 A    6/1998   Maly
(Continued)

FOREIGN PATENT DOCUMENTS

CN            106137532 A   *  11/2016
WO     WO 2002/040095         5/2002
(Continued)

OTHER PUBLICATIONS

U.S. Appl. No. 15/126,775, Peli & Jung, filed Sep. 16, 2016.
(Continued)

*Primary Examiner* — Nay A Maung
*Assistant Examiner* — Daniella M. DiGuglielmo
(74) *Attorney, Agent, or Firm* — Fish & Richardson P.C.

(57) ABSTRACT

A system for providing information about an environment to a user within the environment is featured. An electronic processor is configured to receive input including a user selection of an object of interest from among potential objects of interest. The electronic processor is further configured to provide output to guide the user to move the detection apparatus to position the object of interest near a reference point on a field of view of the detection apparatus, obtain multiple images of the object of interest during the user's movement of the detection apparatus, and crop each of the images to keep the object of interest near a reference point on each of the images.

23 Claims, 12 Drawing Sheets

(51) Int. Cl.
  *H04N 13/271* (2018.01)
  *G06K 9/00* (2006.01)
  *G06K 9/32* (2006.01)
  *A61F 9/08* (2006.01)
(52) U.S. Cl.
  CPC ......... *H04N 13/204* (2018.05); *H04N 13/271* (2018.05); *A61F 9/08* (2013.01); *G06T 2200/04* (2013.01); *G06T 2207/10012* (2013.01); *G06T 2207/10028* (2013.01)
(58) Field of Classification Search
  CPC ............... H04N 13/204; H04N 13/271; G06K 9/00912; G06K 9/3241; A61F 9/08
  USPC ......................................................... 382/154
  See application file for complete search history.

(56) References Cited

U.S. PATENT DOCUMENTS

| | | | |
|---|---|---|---|
| 7,308,314 | B2 | 12/2007 | Havey et al. |
| 7,457,434 | B2 | 11/2008 | Azar |
| 2006/0147197 | A1 | 7/2006 | Spruck et al. |
| 2011/0206291 | A1 | 8/2011 | Kashani et al. |
| 2012/0242801 | A1 | 9/2012 | Barnes |
| 2014/0009591 | A1* | 1/2014 | Ziemeck ............ A61N 1/36046 348/62 |
| 2016/0309137 | A1* | 10/2016 | McNamer ............ H04N 13/221 |
| 2017/0111619 | A1* | 4/2017 | Benosman ............. H04N 9/312 |
| 2019/0070064 | A1* | 3/2019 | Hogle ................ G06K 9/00671 |

FOREIGN PATENT DOCUMENTS

| | | | |
|---|---|---|---|
| WO | WO 2015/143203 | 9/2015 | |
| WO | WO-2017156021 A1 * | 9/2017 | ......... G06K 9/00637 |

OTHER PUBLICATIONS

Aloni & Yitzhaky, Detection of object existence from a single reconstructed plane obtained by integral imaging, IEEE Photonics Technology Letters, 2014, 26(7):726-728.
Aloni and Yitzhaky., "Automatic 3D object localization and isolation using computational integral imaging," Appl. Opt., Aug. 2015, 54(22):6717-6724.
Aloni and Yitzhaky., "Effects of elemental images' quantity on three-dimensional segmentation using computational integral imaging," Appl. Opt., Mar. 2017, 56(8):2132-2140.
Cha et al., "Mobility performance with a pixelized vision system," Vision Research, Jul. 1992, 32(7):1367-1372.
Chen et al., "A quantitative analysis of head movement behaviour during visual acuity assessment under prosthetic vision simulation," Journal of Neural Engineering, Feb. 2007, 4(1):S108-S123.
Davison., "Real-time simultaneous localisation and mapping with a single camera," Proceedings Ninth IEEE International Conference on Computer Vision, Nice, France, 2003, 8 pages.
Gibson et al., "Motion parallax as a determinant of perceived depth," Journal of Experimental Psychology, Jul. 1959, 58(1):40-51.
Goldstein et al., "Medical image communication using halftone algorithms," Proceedings of the Society of Photo-Optical Instrumentation Engineers, 1987, 845:413-418.
Harris., "Focusing On Everything: Light-field cameras promise an imaging revolution," IEEE Spectrum, May 2012, 49(5):44-50.
Hartley & Zisserman, "Chapter 6. Camera Model" in Multiple View Geometry in Computer Vision, Second Edition, Cambridge University Press: Cambridge, UK, 2000, 35 pages.
Jung et al., "Active confocal imaging for visual prostheses," Vision Research, Jun. 2015, 111(PB):182-196.
Jung et al., "Reconstruction of three-dimensional occluded object using optical flow and triangular mesh reconstruction in integral imaging," Optics Express, Dec. 2010, 18(25):26373-26387.
Lange and Seitz, "Solid-state time-of-flight range camera," IEEE Journal of Quantum Electronics, 2001, 37(3), 390-397.
Levoy et al., "Synthetic aperture confocal imaging," ACM SIGGRAPH 2004 Papers, 2004, pp. 825-834.
Lieby et al., "Substituting depth for intensity and real-time phosphene rendering: Visual navigation under low vision conditions," EMBC, 2011, 8017-8020.
Mallat, "Multifrequency channel decompositions of images and the wavelet models," IEEE, 1989, 37(12):2091-2110.
McCarthy et al., "Ground surface segmentation for navigation with a low resolution visual prosthesis," Proceedings of the Annual International Conference of the IEEE Engineering in Medicine and Biology Society, 2011, 4457-4460.
PCT International Preliminary Report on Patentability in International Appln. No. PCT/US18/22916, dated Oct. 1, 2019, 7 pages.
PCT International Preliminary Report on Patentability in International Appln. No. PCT/US2015/021543, dated Mar. 19, 2014, 8 pages.
PCT International Search Report and Written Opinion in International Application No. PCT/US2015/021543, dated Jun. 9, 2015.
PCT International Search Report and Written Opinion in International Appln. No. PCT/US18/22916, dated Jun. 8, 2018, 13 pages.
Peli and Lahav, "Drusen measurements from fundus photographs using computerized image analysis," Ophthalmology, 1986, 93(12), 1575-1580.
Peli, "Simple 1-D enhancement for head-mounted low vision aid," Visual Impairment Research, 1999, 1(1): 3-10.
Saxena et al., "Depth estimation using monocular and stereo cues," In Proceedings of the 20th International Joint Conference on Artifical Intelligence (IJCAI), Jan. 2007, 7:2197-2203.
Schiller & Tehovnik., "Visual Prosthesis," Perception, Oct. 2008, 37(10):1529-1559.
Shin et al., "Optical flow-based real-time object tracking using non-prior training active feature model," Real-Time Imaging, Jun. 2005, 11(3):204-218.
Stern and Javidi, "Three dimensional sensing, visualization, and processing using integral imaging," Proceedings of IEEE, Special Issue on 3D Technologies for Imaging and Display, 22006, 94(3):591-607.
Sun et al., "Secrets of optical flow estimation and their principles," in Proceedings of IEEE Conference on Computer Vision and Pattern Recognition (IEEE, 2010), 2432-2439.
Zhou et al., "Object tracking using SIFT features and mean shift," Computer Vision and Image Understanding, Mar. 2009, 113(3):345-352.

* cited by examiner

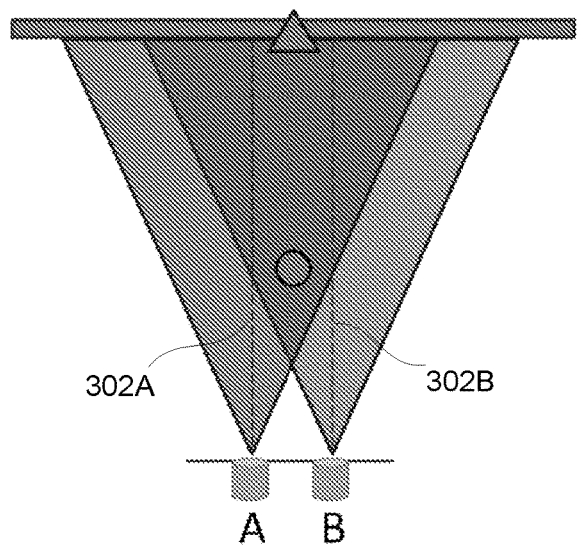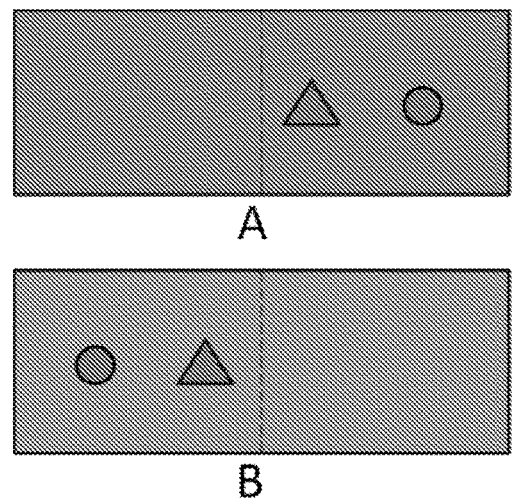
FIG. 2A FIG. 2B
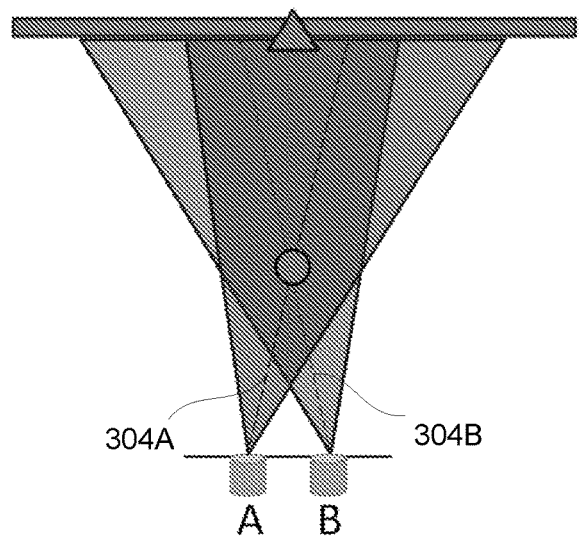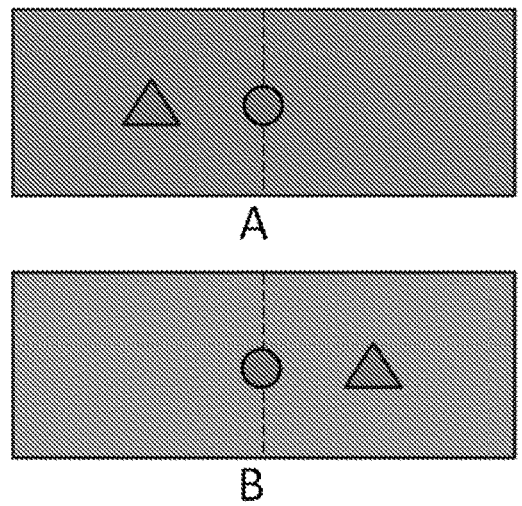
FIG. 2C FIG. 2D

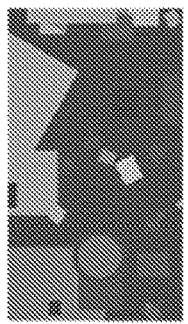
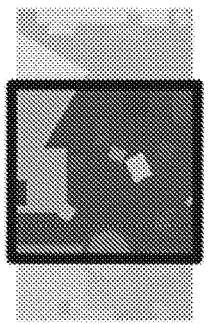
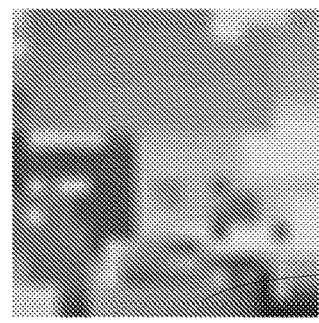
*Camera views with head movements*
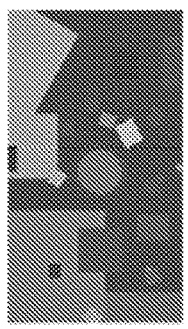
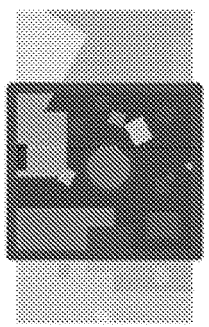
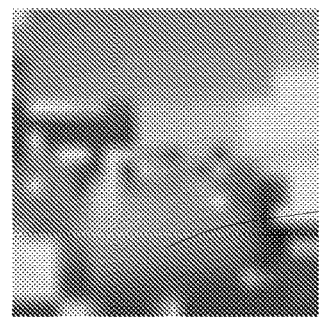
*Prosthetic VF*
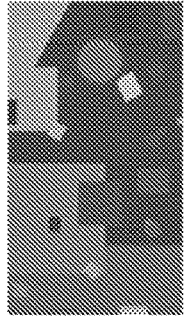
FIG. 8A
FIG. 8B    FIG. 8C    FIG. 8D
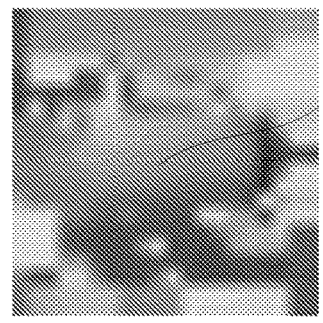
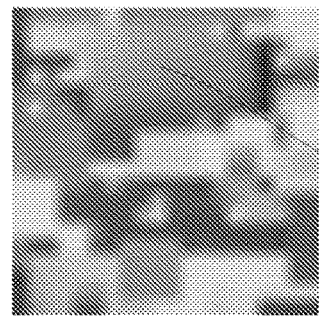
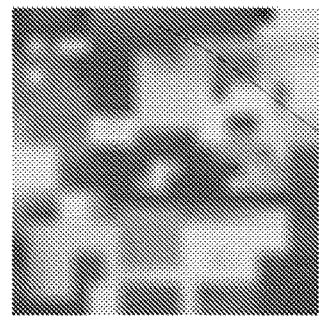
FIG. 8E

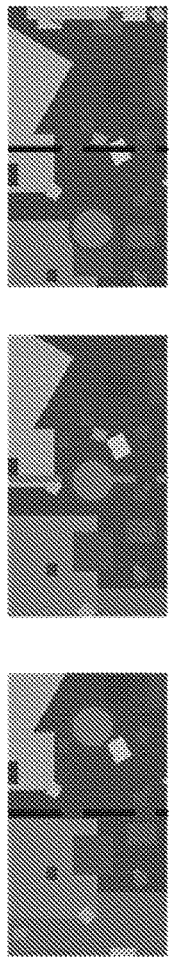
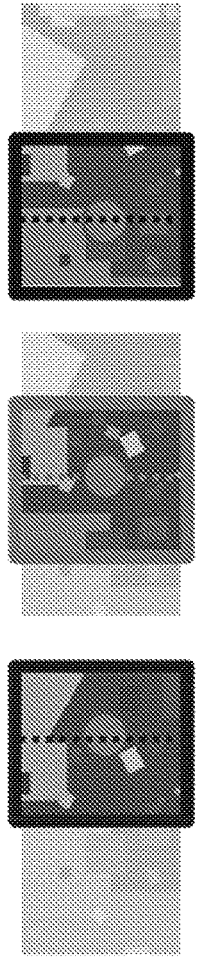
Camera views with head movements
Prosthetic VF with compensatory cropping
FIG. 9B   FIG. 9C   FIG. 9D
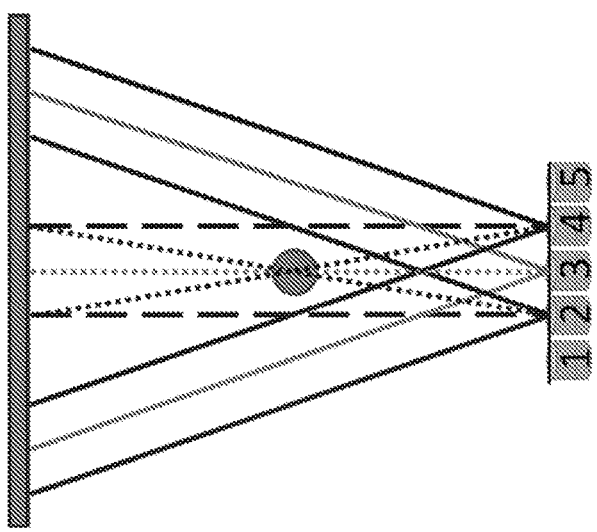
FIG. 9A
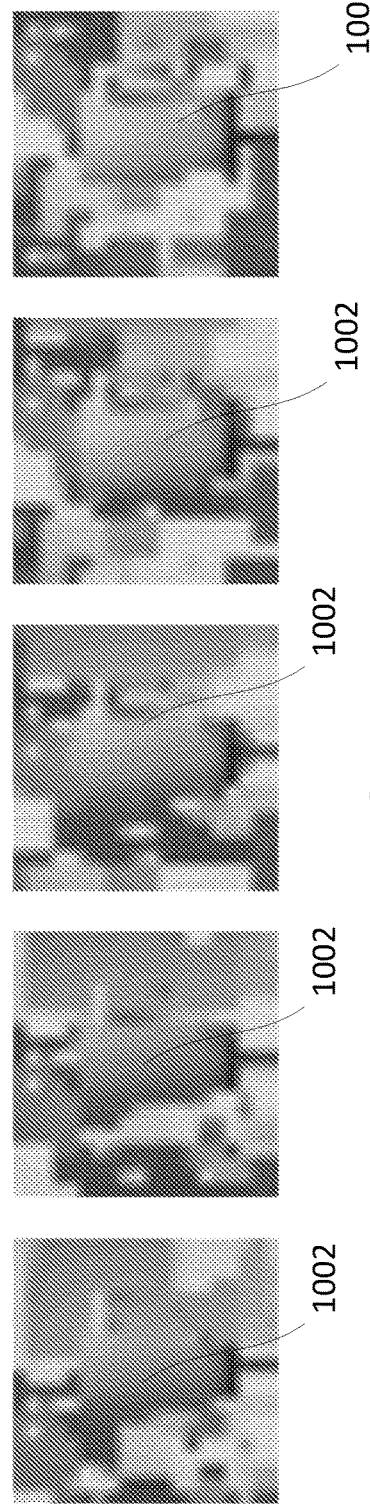
FIG. 9E

MOTION PARALLAX IN OBJECT RECOGNITION

STATEMENT AS TO FEDERALLY SPONSORED RESEARCH

The inventions described herein were made with Government support under Department of Defense grant number W81XWH-16-1-0033. The Government has certain rights in the inventions.

TECHNICAL FIELD

This disclosure relates to imaging systems and methods to address visual impairment and rehabilitation.

BACKGROUND

According to the World Health Organization, an estimated 39 million people worldwide are blind. In the United States, 1.2 million people are legally blind and ~10% of them are functionally blind. Their numbers are projected to grow in the coming decades. Although blind people can access text through braille and text-to-speech, mobility indoors and outside is limited, dangerous, and largely depends on the long cane. Blindness also limits numerous other activities of daily living, particularly tasks requiring visual search and object recognition. As a result, many pursuits (vocational and social) are limited, especially for the acquired blind whose blindness occurs in adulthood. Restoration of vision through prostheses for restoring functional vision in blind users may address many of these difficulties.

SUMMARY

The systems and methods disclosed herein use motion parallax to provide reliable depth cues for rendering images with a cluttered background for artificial vision, e.g., prosthetic or computer vision or visual sensory substitution devices, and thus improve object recognition. Most prosthetic visual devices use a head-mounted video camera to acquire high-resolution images and convert those images to a low resolution and low dynamic range format for electrodes to display on a user's sensory receptors, such as on the, skin, tongue, retina, and/or visual cortex. Due to the low resolution, the utility of current devices is limited especially when video signals from a cluttered environment are merged together.

In one aspect, systems for providing information about an environment to a user within the environment include a detection apparatus configured to obtain depth and image information about the environment, and an electronic processor in communication with the detection apparatus. The depth and image information includes data relating to potential objects of interest at multiple distances relative to a position of the user within the environment. The electronic processor is configured to obtain, from the depth and image information, a set of one or more depth planes containing the potential objects of interest, and receive input including a user selection of an object of interest from among the potential objects of interest. The electronic processor is further configured to provide output to guide the user to move the detection apparatus to position the object of interest near a reference point on a field of view of the detection apparatus, obtain multiple images of the object of interest during the user's movement of the detection apparatus, and crop each of the images to keep the object of interest near a reference point on each of the images.

In another aspect, the disclosure features methods of providing information about an environment to a user within the environment that include obtaining, using a detection apparatus, depth and image information about the environment. The depth and image information includes data relating to potential objects of interest at multiple distances relative to a position of the user within the environment. The methods further include obtaining, from the depth and image information, a set of one or more depth planes containing the potential objects of interest to the user, and receiving input including a user selection of an object of interest from among the potential objects of interest. The methods further include providing output to guide the user to move the detection apparatus to position the object of interest near a center of a field of view of the detection apparatus, obtaining multiple images of the object of interest during the user's movement of the detection apparatus, and cropping each of the images to keep the object of interest near a center of each of the images.

Certain implementations of the systems and methods can include one or more of the features described below and elsewhere herein.

In some implementations, the systems further include motion sensors. The motion sensors can be configured to measure motions and displacements of the detection apparatus. The motion sensors can be configured to measure an initial position of a head of the user when the user selects the object of interest. The electronic processor can be configured to provide output to guide a lateral shift of a head of the user to adjust a position of the field of view, and the motion sensors can be configured to measure a distance of the lateral shift relative to the initial position of the head.

In some implementations, the methods further include detecting motions and displacements of the detection apparatus. The methods can further include providing an output to guide a lateral shift of a head of the user to adjust a position of the field of view, and measuring a distance of the lateral shift of the head relative to an initial position of the head.

In some implementations, the electronic processor is configured to adjust a position of the field of view by a distance substantially matching a distance of a lateral shift of a head of the user. The electronic processor can be configured to calculate a principal rotation angle of a principal ray for the object of interest from the head after the lateral shift, and a distance of the object of interest from the detection apparatus. The electronic processor can be configured to crop each of the images based on the principal rotation angle and present each resulting cropped image to the user.

In some implementations, the methods further include adjusting a position of the field of view by a distance substantially matching a distance of a lateral shift of a head of the user. The methods can further include calculating an angle representing a principal rotation angle of a principal ray for the object of interest from the head after the lateral shift.

In some implementations, the electronic processor is configured to identify portions of the images that correspond to the object of interest by identifying a feature of the object of interest, and cropping each of the images such that the object of interest is near the center of the each of the images. The electronic processor can be configured to present each resulting cropped image to the user. In some implementations, cropping each of the images includes cropping each of the images based on the principal angle of the principal ray, and presenting each resulting cropped image of the object of interest to the user.

In some implementations, the methods further include identifying portions of the images that correspond to the object of interest by identifying a feature of the object of interest, and cropping each of the images such that the object of interest is near the center of each of the images. In some implementations, the methods further include presenting each resulting cropped image to the user.

In some implementations, the detection apparatus includes a depth camera system including one or more of a light-field camera, stereo camera, IR-based depth camera, or a multiple camera array.

In some implementations, the depth and image information includes a set of depth sliced images each corresponding to a depth plane at a different distance relative to the position of the user. The depth sliced images can include confocal images.

In some implementations, the one or more depth planes are positioned at one or more distances relative to the position of the user within the environment. The one or more distances can be within a range bounded by a minimum distance value. In some implementations, the one or more depth planes are positioned at one or more distances relative to the position of the user within the environment. The one or more distances can be within a range bounded by a maximum distance value.

In some implementations, the electronic processor is configured to obtain the one or more depth planes by determining an operating mode associated with the system. In some implementations, the electronic processor is further configured to convert the images into electrical signals, and to transmit the electrical signals to a visual prosthesis worn by the user.

In some implementations, the methods further include converting the images into electrical signals, and transmitting the electrical signals to a visual prosthesis worn by the user.

In some implementations, the systems further include an input interface configured to receive input information from the user and to transmit the input to the electronic processor based on the input information. The input interface can include a controller mounted to a cane. The input interface can include a voice-activated interface. In some implementations, the controller is configured to track the object of interest in a depth plane. In some implementations, the reference point on the field of view is a center of the field of view, and the reference point on each of the images is a center of each of the images.

In another aspect, the disclosure provides methods carried out by the systems described and illustrated herein, and described in further detail below.

Embodiments of the systems and methods disclosed herein also include all of the other features or steps disclosed herein, including features or steps disclosed in connection with different embodiments, in any combination as appropriate.

As used herein, the term "field of view" or "FoV" means the field of view of an image detection device, such as an optical sensor, a camera, a depth camera, or other appropriate image detection device.

As used herein, the term "visual field" or "VF" means the visual field displayed by a visual prosthetic device or sensory substitution device stimulator to the user.

As used herein, the term "camera" can refer to any image capturing device, including video cameras.

As used herein, the term "depth camera" can refer to any device that can capture depth information, including a stereo camera, IR-based depth camera (structured light or time-of-flight), light-field camera, multi camera array, or other appropriate device that can capture depth information.

The new systems and methods provide several advantages, including improved clarity of objects of interest (OIs) to a user of a prosthetic visual system. Compared to systems that do not implement the methods disclosed herein, the systems and methods disclosed herein can reduce interpretation times significantly and permit more active exploration of a user's environment. The user can more easily interact with the environment and more easily visually discern objects in the environment.

In the present disclosure, various embodiments are discussed for purposes of illustration. In general, however, the features and steps associated with the various embodiments are not specific to those embodiments unless otherwise noted, and can be combined with other features and steps. Accordingly, the present disclosure is not limited to the specific combinations of features and steps described, but also encompasses other combinations of the features and steps disclosed herein, except where indicated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIGS. 2A-2D are schematic diagrams showing apparent motion of relatively close and distant objects due to the lateral motion of a viewer (FIGS. 2A and 2B) or due to the lateral motion and simultaneous eye rotation of a viewer (FIGS. 2C and 2D).

FIGS. 8A-8E are drawings illustrating a field of view and resulting visual field of typical prior art prosthetic visual devices as the field of view translates laterally.

FIGS. 9A-9E are drawings illustrating a field of view and resulting visual field of prosthetic visual devices and methods described herein as the field of view translates laterally.

Like reference symbols in the various drawings indicate like elements.

DETAILED DESCRIPTION

Figure 1:
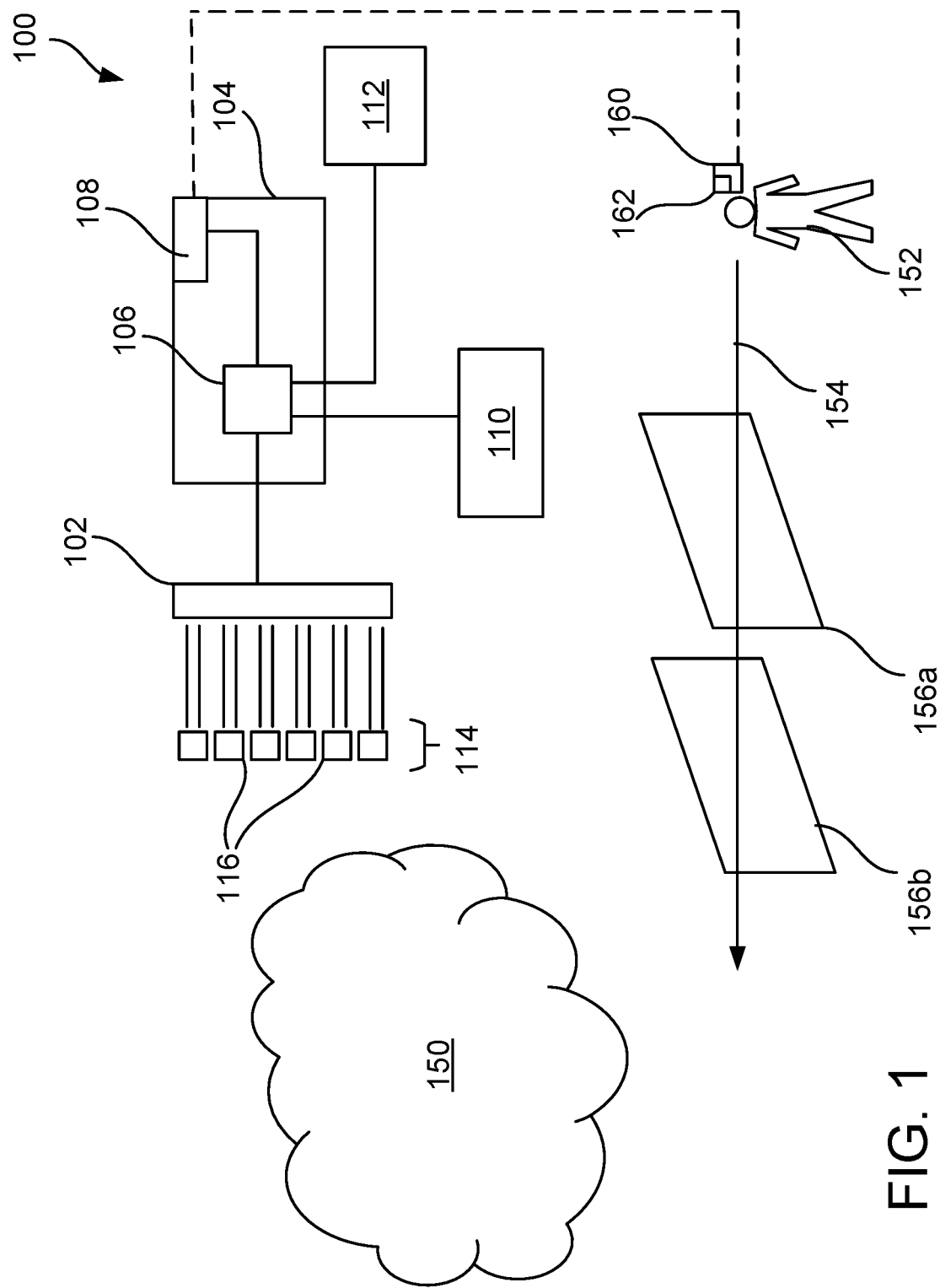
FIG. 1 is a schematic diagram of an embodiment of an imaging system.

The systems and methods disclosed herein acquire and crop video camera images around a foreground OI to stabilize the OI at a reference point on a visual field of a viewer, such as a center of the visual field, a center of a quadrant of the visual field, a predefined location on the visual field, or other appropriate reference point. These systems and methods enable the user to take advantage of motion parallax in visually distinguishing the OI (no motion with head movement) from background clutter (motion corresponding with head movement) such that the OI does not move and the background clutter moves with head movement. These systems and methods thus improve object recognition for video-based artificial vision, e.g., prosthetic vision or visual sensory substitution devices.

Most prosthetic visual devices use a head-mounted video camera to acquire high-resolution images and convert those images to a low resolution and low dynamic range format for electrodes to display on a user's sensory receptors, such as on the tongue, retina, and cortex. Due to the low resolution, the utility of current devices is limited especially when video signals from a cluttered environment are all merged together. The applicability of motion parallax in prior systems to improve object recognition has been limited due to the lack of a vestibular-ocular reflex like mechanism in such systems to stabilize the OI at the center of visual field in the narrow visual field of these systems. In the systems described herein, these limitations are overcome by dynamically cropping camera images around the OI and thus repositioning the OI proximate a reference point in the images, e.g., a center of the images, a center of a quadrant of the images, a predefined location on the images, or other appropriate reference point in the images. This process can mimic the function of the vestibular ocular reflex in normal vision. The proposed systems achieve stable OI representations at the center of the visual field while cluttering detail from other depth planes are presented with varying levels of motion when the user undertakes lateral head movement.

This disclosure features systems and methods for providing to a user information about the user's environment. In particular, for vision-impaired users, e.g., severely vision-impaired (e.g., totally blind or functionally blind) users, the information can be provided in the form of image data that is converted to electrical signals and delivered to a visual prosthesis. Information can also be provided in the form of other signals, including haptic signals (e.g., vibrations, movements, and other tactile signals) and auditory signals. For some prostheses, the information can include visual or nonvisual information (e.g., infrared images) provided through a head-mounted display (HMD). Visual prostheses using an additional camera system can use the featured systems.

The processing techniques described herein apply image processing techniques or depth camera system to suggest and select image information corresponding to in-plane objects (e.g., objects at selected distances or within particular focal planes relative to the user's position) from out-of-plane objects to effectively stabilize the object at the center of view and actively moving background clutter in the other planes. The image information provided to the user therefore represents the in-plane objects largely stable while moving the others, and is presented in a compressed (e.g., reduced resolution and reduced dynamic range) format suitable for retinal implants or other visual prostheses, including sensory substitution devices.

First, the user can select the image information to be displayed to the user by scanning and traversing through images in different depth, selecting a depth plane from among multiple proposed depth planes that includes a potential OI, and then moving the user's head or a detector of the system according to instructions from the system (e.g., that request the user to move their head laterally or move a detector of the system laterally to bring the OI to the center of the system's visual field). Meanwhile, the proposed stabilization system can mimic natural eye movement and thus can provide visual cues to separate the OI from the moving background. In particular, the OI can be stabilized at the center of visual field or other reference point on the visual field while the background moves relative to the center or the reference point. A conventional head-mounted camera of the visual prostheses may not be able to lock the OI at the center of the view or the reference point, and the user's head movement may easily move the OI out of the visual field. In contrast, with the proposed system, the movement of the user's head with the proposed stabilization system takes advantage of motion parallax to provide reliable de-cluttering visual cues (e.g., by stabilizing the OI such that the OI is static in front of moving background clutter) for rendering images for prosthetic vision with a cluttered background and thus improve object recognition.

Imaging Systems

FIG. 1 is a schematic diagram showing an embodiment of an imaging system 100 for providing depth information about a user's environment to a user. An example of such an imaging system is described in International Application Number PCT/US2015/021543, the entire contents of which are incorporated herein by reference. A confocal imaging system is one example of a depth imaging system that could provide depth information about the user's environment to the user. In other embodiments, rather than being a confocal imaging system, the imaging system 100 of FIG. 1 could include another type of depth imaging system, such as, for example, a stereo camera, an IR depth camera (e.g., a time of flight camera or a structured light camera), a light-field camera for depth maps, a multiple camera array, or another appropriate depth imaging system.

The imaging system 100 includes a depth detector 102 coupled to a control unit 104. The control unit 104 includes an electronic processor 106 and, optionally, a signal transmitter 108 coupled to the processor 106. Also included in the imaging system 100 are an optional input interface 110 and an optional output device 112, both of which are coupled to the electronic processor 106.

In general, the detector 102 is configured to obtain depth information, e.g., indicative of a depth relative to the user, about the environment 150 of a user 152 of the imaging system 100. In general, the depth information corresponds to objects' distance information from a position of the user 152 within the environment 150 or from a position of the detector 102 within the environment 150. As shown schematically in FIG. 1, the depth information corresponds to information obtained at one or more different depth planes 156a and 156b positioned along axis 154, which extends in a direction outward from the user 152.

In general, in this embodiment, the imaging system 100 corresponds to an imaging system using any depth cameras as described herein. Conventional confocal imaging systems acquire depth planes that each correspond to a relatively shallow depth resolution, while contributions from objects located outside the depth resolution range are suppressed entirely. In some embodiments, the depth information acquired by the imaging system 100 can include a set of confocal images of the environment 150 acquired by, for example, a light-field camera or IR-based depth camera (structured light or time-of-flight camera). Each of the depth planes captured by the depth camera can correspond to a different distance along axis 154 relative to the user 152.

In certain embodiments, the imaging system 100 can obtain depth information corresponding to different distances from the user 152 in a single depth image frame. To obtain the depth information in this manner, the imaging system 100 can include a two-dimensional array 114 of lenses (light-field camera), depth sensors (IR-based depth camera), or cameras (multiple camera array) 116, as shown in FIG. 1. Because the detector 102 is generally worn or carried by the user 152, depth planes, e.g., 156a and 156b, in front of the user are also located at different distances along axis 154 relative to the position of the user 152.

The imaging system 100 can also include a variety of other imaging components. For example, the imaging system 100 can include one or more lenses, stops, filters, beam splitters, diffractive elements, apertures, spatial modulators, and mirrors. While the imaging system 100 has been described as directing and re-directing light, in other embodiments, the imaging system 100 can emit other radiation or signals that can interact with the environment and detect features of the environment. For example, the imaging system 100 can emit radiofrequency waves, ultrasonic waves, infrared light, or other waveforms. The imaging system 100 can also have magnifying or minifying optics (lens set) in front of the array 114 to enlarge or shrink the images formed by the imaging system 100.

As shown in FIG. 1, the imaging system 100 can optionally include a signal transmitter 108 coupled to the electronic processor 106. In some embodiments, the signal transmitter 108 is configured to transmit electrical signals (wirelessly or through conductors) to a visual prosthesis 160 worn by the user 152 of the system 100. The prosthesis 160 can have included motion sensors 162 mounted to the prosthesis and worn by the user 152. In general, the imaging system 100 can be used with a wide variety of different types of visual prostheses, and the signal transmitter 108 can be configured to deliver electrical signals that are compatible with each such prosthesis. As one example, the signal transmitter 108 can transmit signals that are compatible with retinal implants positioned within an eye of the user.

During operation of the imaging system 100, the electronic processor 106 generates one or more images for transmission to the visual prosthesis 160. The images are then converted by the processor 106 and/or the signal transmitter 108 into electrical signals suitable for the prosthesis, and transmitted by the signal transmitter 108 to the prosthesis. Where the imaging system 100 does not include the transmitter 108, images can be converted into electrical signals by the processor 106, which then transmits the signals directly to the prosthesis.

The imaging system 100 can optionally include an input interface 110. The input interface 110 allows the user to transmit information and instructions to the imaging system 100, which are then used to adjust the operating parameters of the imaging system 100. A variety of different interfaces can be used, including tactile interfaces (e.g., touch-sensitive interfaces, buttons, switches, and knobs) and voice-activated interfaces (e.g., a microphone for receiving auditory instructions from the user). The imaging system 100 can include wireless control (e.g., Bluetooth or WiFi) to allow the user to control the imaging system 100 without the use of a direct wired connection. To allow the user to direct the imaging system 100 to particular objects within the user's environment, the input interface 110 can include sensors such as gyroscopes, accelerometers, touch pads, and knobs that allow the user to select objects through gesture-based movements such as nodding of the head and hand motions.

The input interface 110 can be mounted in a variety of ways to permit the user to conveniently and accurately deliver information and instructions to the imaging system 100. In some embodiments, for example, the input interface 110 can be integrated into the handle of a long cane typically carried by the blind user, allowing the user to deliver instructions to the system with relatively slight, unobtrusive hand and/or finger movements. In some embodiments, the input interface 110 can be integrated into one or more articles of clothing or jewelry (e.g., a ring, bracelet, glove, necklace, pin, pendant, or eyeglass frames).

The imaging system 100 can also optionally include an output device 112. The output device 112 is generally configured to convey information to the user in the form of warning or alerting signals that draw the user's attention to objects in the user's environment. Such signals can be delivered to the user via the output device 112 when, for example, an object closely approaches the user, or when an object is detected. A variety of different signals can be provided to the user, including for example tactile signals and auditory signals. Accordingly, the output device 112 can be implemented in variety of ways depending upon the nature of the signals to be delivered. In some embodiments, output device 112 can include a vibrating annunciator or another device configured to deliver tactile signals to the user. In certain embodiments, the output device 112 can include a speaker or other sound generating device for delivering auditory signals to the user. For example, bone conducting speakers are well suited for such applications, as they leave the natural hearing of a vision-impaired user unimpeded.

Implementation of Motion Parallax

In normal vision, motion parallax, as a monocular cue, is used to separate signals from different depths according to different amount of movement induced by change of viewpoint. FIG. 2A shows an example in which two objects (e.g., potential OIs), a circle and triangle, are located at different distances from the viewer who gazes straight ahead (towards infinity). The circle represents an object relatively close to the viewer, while the triangle represents an objective relatively distant to the viewer. The viewer gazes along the viewing direction represented by a principal ray 302A when the viewer is at position A, and gazes along a viewing direction represented by a principal ray 302B when the viewer moves to position B (neglecting binocular vision for simplicity). Since the viewer is gazing straight ahead toward infinity, both objects are not OIs, but clutter. Referring also to FIG. 2B, when moving from position A to position B, the viewer sees the triangle moving from right to left. The viewer also sees the circle move from right to left but by a larger distance than the triangle, since the circle is closer to the viewer than the triangle along both principal rays 302A, 302B. This difference in apparent movement, or motion parallax, is the same effect that causes car passengers to perceive distant objects as moving past more slowly than closer objects and serves as a powerful depth cue in normal vision.

In contrast to the views shown in FIGS. 2A and 2B of distance viewing, when the viewer is observing an OI that is typically closer to the viewer, the viewer generally moves their head (and/or their body) with eye rotation to place the OI (e.g., the circle in FIG. 2C) along their principal ray to better distinguish the OI from the environment (e.g., the triangle in FIG. 2C). Referring to FIG. 2C, rather than gazing into the far distance or toward infinity, the viewer looks at the circle (the OD with eye rotation along the principal ray 304A when at position A. When the viewer moves to position B, the viewer keeps their gaze on the OI (circle) along principal ray 304B, keeping the OI in their central field of view while other clutter (triangle) is moving. This rotation of the eye with head translation leads to a stable presentation of the circle at the center of both images, as shown in FIG. 2D, while the farther triangle appears to move across the viewer's view.

This viewing strategy in normal vision is useful as the viewer maintains visual contact with the OI and takes advantage of motion parallax to distinguish the OI from clutter existing in other depth planes (e.g., the plane of the triangle). Although the differential movement between the triangle and circle objects is not changed between FIG. 2B and FIG. 2D, it is much easier to separate the centered circle OI in FIG. 2D from the background clutter because the clutter is moving but not the circle M.

Methods of Use

The imaging system 100 uses a guided-cropping system to optimize motion parallax cues by stabilizing the OI at the center of view and moving background clutter for object recognition in a visual prosthesis. In some implementations, the imaging system 100 can be incorporated as a selective mode in a visual prosthetic device 160 for recognizing objects in the environment 150 around the user 152. This functionality keeps users informed by giving them options to activate the capability and actively select a particular depth or OI. The system can be described in three modules: Module I, which generates images used to identify OI and the depth planes at which those objects are located relative to the user; Module II, which directs the user to place a selected OI in the center of the field of view (FoV) of the detector 102; and Module III, which directs the user's head movements to enable compensatory cropping to stabilize on the selected OI and present it more clearly for inspection by the user.

Figure 3:
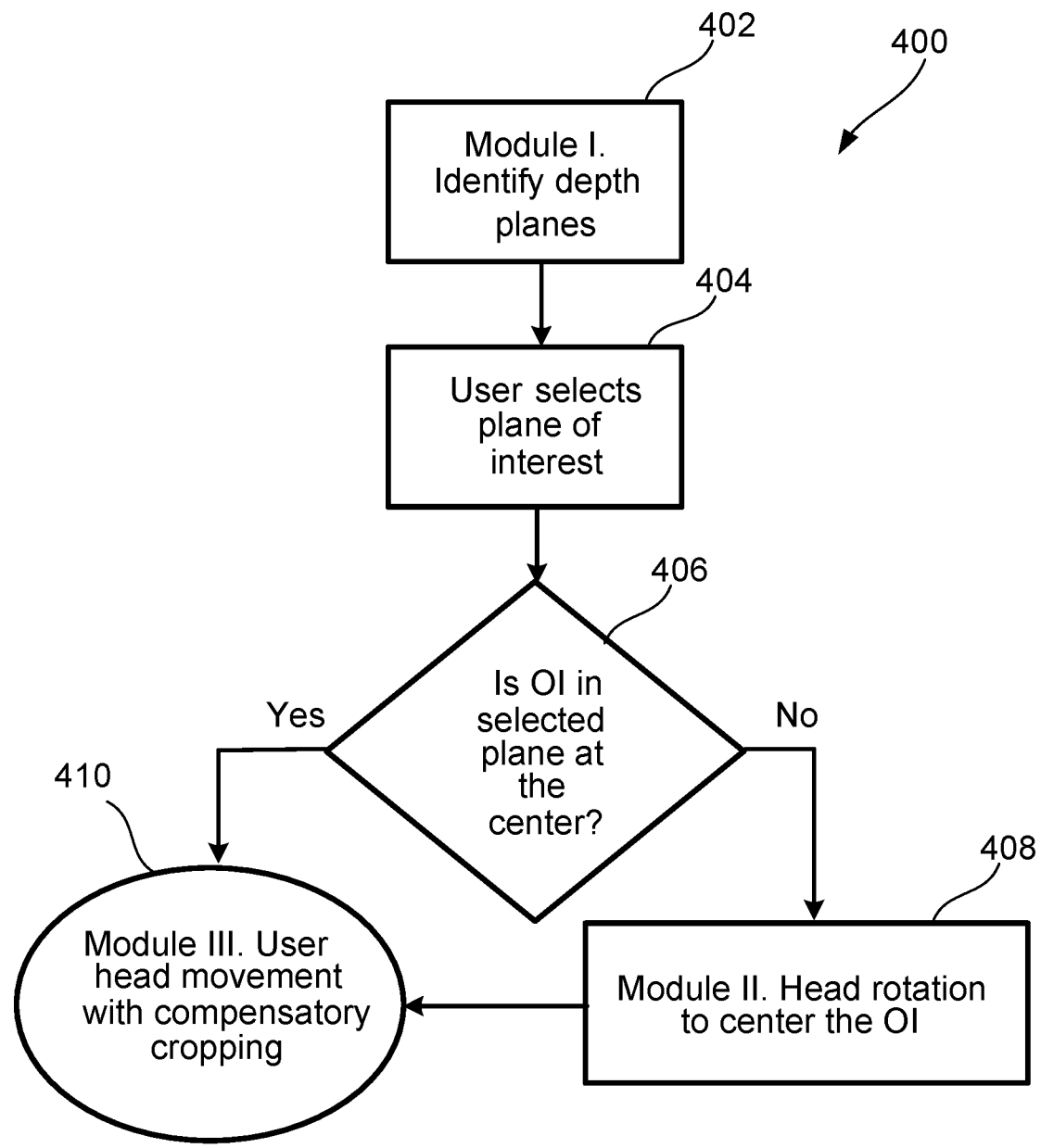
FIG. 3 is a flow chart showing a series of steps for delivering information about a user's environment to the user using an imaging system.

FIG. 3 shows a flowchart 400 that includes a series of steps that the imaging system 100 uses to deliver information about a user's environment 150 to the user 152 once the system is activated. In the first step 402, the processor 106 identifies and suggests a pool of depth planes to the user 152 that have potential OIs based on the images received on the detector 102 as described above. Next, in step 404, the user selects one depth of interest from the pool of depth planes, e.g., one depth plane selected from a pool of five OI/depths. The user 152 can manually select one or more focal planes corresponding to different distances by activating controls on the input interface 110 (e.g., touch pad, slide bar, knob controller, etc.), and/or by issuing a speech command that is detected by the input interface 110 and recognized by processor 106. In some instances, the system can inform the user 152 via the output device 112 how many OIs are available, and which OI is being considered at any given time. In some examples, these different OIs can be examined one at a time, starting with the closest object.

The processor 106 then determines, at step 406, if the OI contained in the selected depth plane is located in the center of the FoV of the detector 102. If the OI is not centered, at step 408, the processor 106 executes the system module that directs the user 152 to rotate his head to center the OI in the FoV. If the OI is centered at step 406, or once the OI is centered after step 408, at step 410, the processor 106 then executes the system module to lock the OI at the center of view even with the user's head movement to enable parallax-driven compensatory cropping and presentation of the OI with the moving background clutter following head movement at step 410. While described as being centered in steps 406 and 408 and in other certain implementations herein, in other implementations, the OI is not centered but rather is positioned proximate another reference points besides a center of the FoV. For example, the reference point can correspond to a center of a quadrant of the FoV, a predefined point on the FoV, or other appropriate reference point.

Module I: Identification and Suggestion of Depth Planes of Interest

Module I includes steps 402 and 404 of FIG. 3, and requires that the imaging system 100 capture the depth information of the environment 150 in front of the user 152. In some implementations, depths can be determined by using a depth camera such as a structured light camera (e.g., Kinect, Microsoft, Redmond, Wash.), a time-of-flight camera, a light field camera, a stereo camera, or a multiple camera array on a head-mounted video camera system.

In some embodiments, this depth information can be calculated by tracking the user's head movement and recording corresponding video image movement with the aid of the motion sensors 162 (accelerometer and gravity sensor) attached to a head-mounted video camera system. When the user 152 triggers the function, the imaging system 100 provides the user with an instruction to make a lateral head shift (or left-and-right motion). During the head shift, the imaging system 100 captures different views while measuring head translation by the sensors. The amount of feature shift is acquired using feature matching methods (e.g., optical flow, SIFT or scale-invariant feature transform, etc.) that compare multiple viewpoints captured during the user's head translation (include stereo matching). The depth map is then calculated by triangulation.

After obtaining the depth information using one of above-mentioned or another method known in the art, the imaging system 100 identifies the pool of depth planes that have potential OIs in step 402. As one example, the imaging system 100 can divide an image at a particular depth plane into multiple sections (depth resolution) and calculate the density of pixels in each section. After normalizing the number of pixel in each section by the image resolution, a histogram of number of pixel in each section with potential peaks is determined. The section that has the highest pixel density may be a potential location of the OI. Other possible methods that can suggest the potential depth planes for objects of interest using the depth information can be applied in this system. Once detected, the user 152 can choose among the identified planes of interest for closer observation, and the processor 106 can proceed to step 406 in FIG. 3 and then to Module II to guide the user to center the OI in the FoV at step 408 if necessary.

Module II: Guided Head Rotation

An optimal performance requires that the user 152 start from a position with the OI at the center of the detector's FoV. Thus, given the depth plane and related OI selected at step 404, the processor 106 then decides whether the OI in that depth plane is located near the center of the FoV, step 406, and guides the user 152 to step 408 if it is not. The user 152 first adjusts his head rotation and follows with body rotation to align his body with the direction of the object so that the lateral head movement is in a direction orthogonal to a line connecting the initial head position and the OI.

Figure 4:
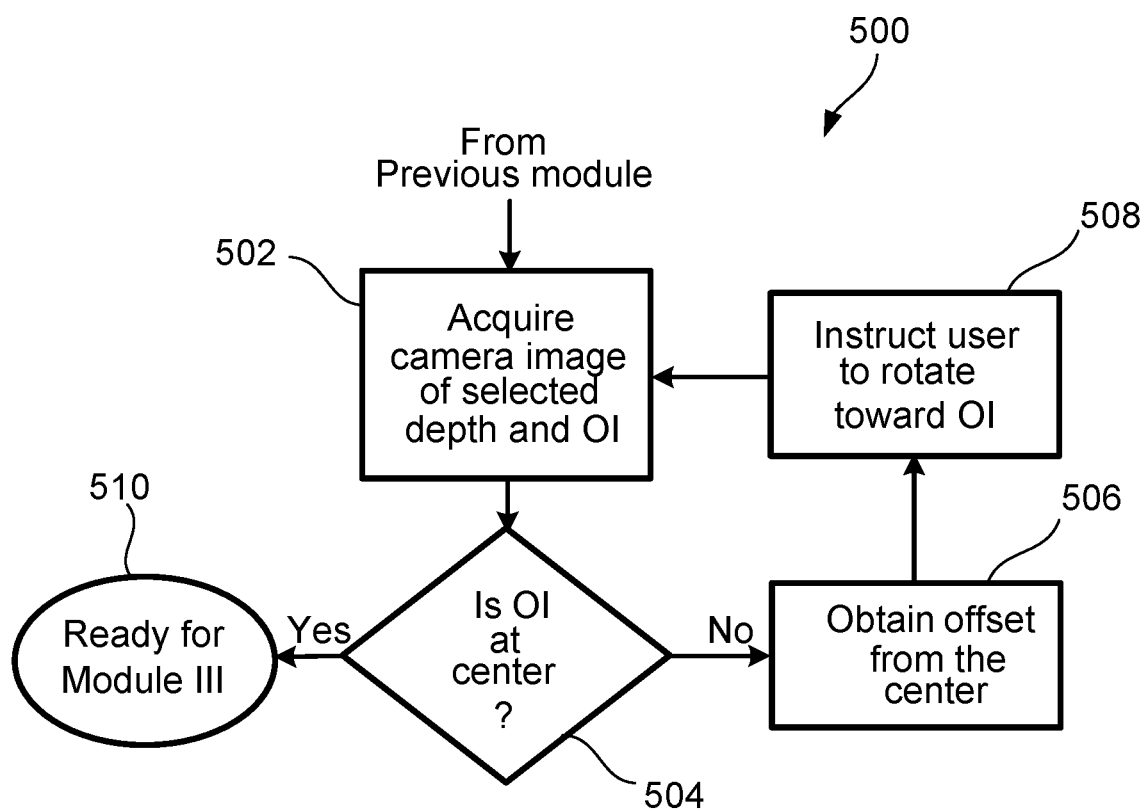
FIG. 4 is a flow chart showing a series of sub-steps for delivering information about a user's environment to the user using an imaging system.

FIG. 4 shows a flowchart 500 showing the details of step 408, implementation of system Module II, which directs the user 152 to rotate his or her head to center the OI in the detector FoV. At step 502 the processor 106 loads the detector 102 image corresponding to the selected depth and has identified the location of the OI as part of the user selection step 404 in FIG. 3. The processor 106 checks if the selected OI is near the center of the FoV at step 504 (equivalent to step 406 in FIG. 3). If the object is centered, the processor 106 at step 510 moves the object identification to Module III for the compensatory cropping.

Figure 5A:
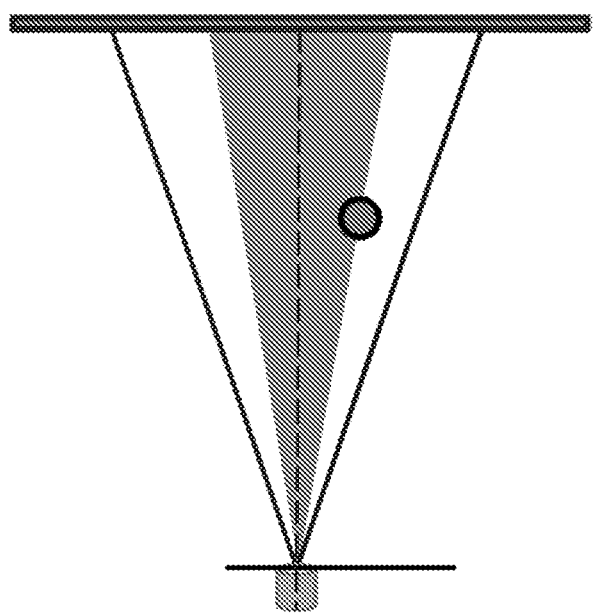
FIGS. 5A and 5B are schematic drawings illustrating some of the sub-steps of FIG. 4.

Frequently, at step 504 the OI is not centered in the image, as illustrated in FIG. 5A. The system therefore moves to step 506 and calculates the offset of the OI from the center of the image. The system then guides the user to rotate his head to aim at the OI and place it along the principal ray of the detector 102, as shown in FIG. 5B.

There are multiple ways to give a user 152 feedback for head rotation toward the OI via the output device 112, such as visual, auditory, haptic, or a combination. For example, flashing electrodes on the left or right side in the visual prosthesis image can guide the direction of head rotation, or vibrational or electrical feedback contacts in left and right hands or arms can provide guidance. An audio cue could present as a sound from the left indicating a left rotation, a sound from the right indicating a right rotation, and the magnitude corresponding to the required rotation amount. In some implementations, the flashing (or vibration or electrical or other feedback) can change in frequency and/or intensity as the center of the FoV moves closer to the OI. For example, the flashing can get slower or faster the closer or further the OI is from the prosthetic image center.

Figure 5B:
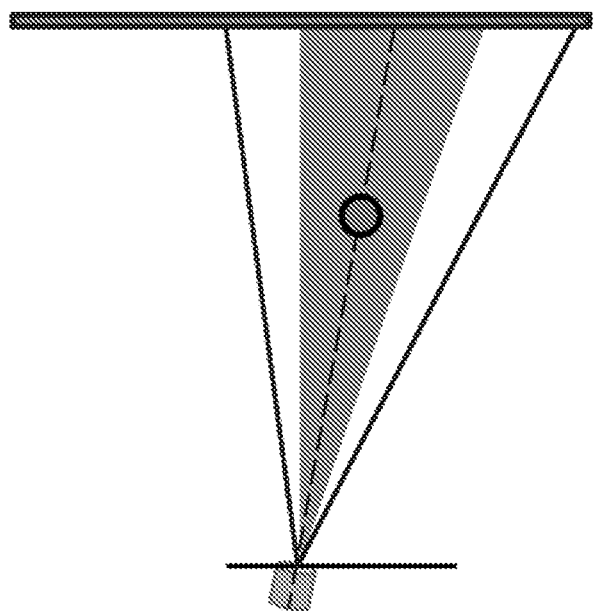

As the user 152 rotates (e.g., both head and body) in response to the feedback, the OI location is constantly measured and updated (cycling through steps 502, 504, 506, and 508 in FIG. 4) and the guiding feedback stops when the OI is near the detector FoV center, as shown in FIG. 5B. In some implementations, an additional signal (e.g., cessation of flashing, or a unique vibration, or sound cue) can confirm to the user 152 that the OI is now in the center of the FoV.

Once the OI is centered in the detector FoV, at step 510 the user (now facing the OD is instructed to utilize a natural lateral head movement to explore the OI, which is centered during the head movement by using image cropping, or move to Module III.

Module III: Image Cropping with Head Translation

Figure 7A:
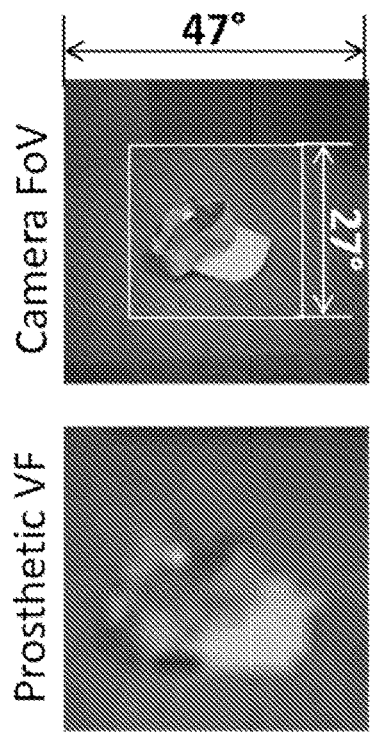
FIGS. 7A-7D are schematic drawings illustrating sub-steps of FIG. 6.

For the background decluttering by motion parallax using head movements, the system 100 should track and dynamically crop around the OI to maintain it at the center of the prosthetic VF during the head translation. This is of particular advantage in prosthetic vision where the VF of the prosthesis 160 is generally extremely limited compared to the FoV of the detector 102. A typical visual prosthetic VF is around 20°, while the detector FoV can be as wide as 50° to 80°. For example, in FIG. 7A the camera FoV is 47° and the prosthetic VF is 27° indicated by the box).

Two methods to calculate the area for the cropping are described: image cropping calculated according to information acquired through head tracking sensors and acquiring the area to crop based on feature matching.

Head Tracking Sensors

Figure 7B:
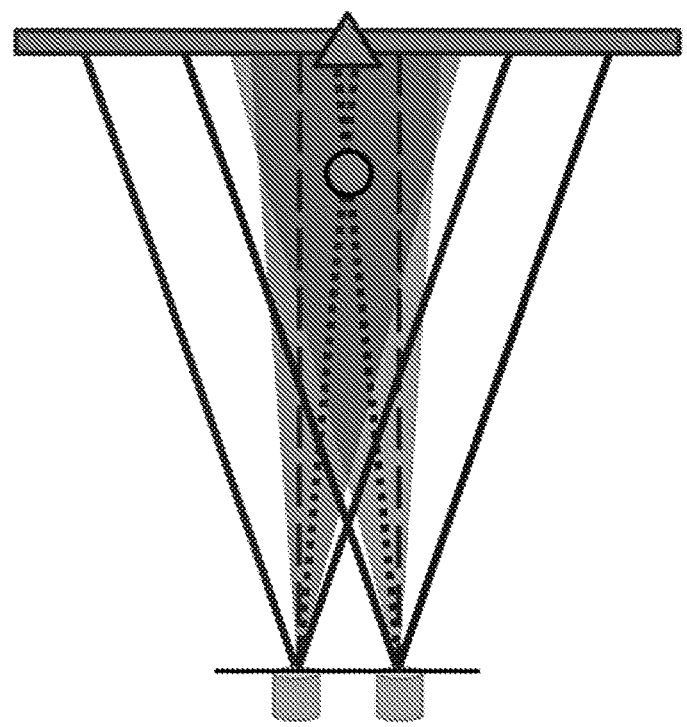
Figure 7C:
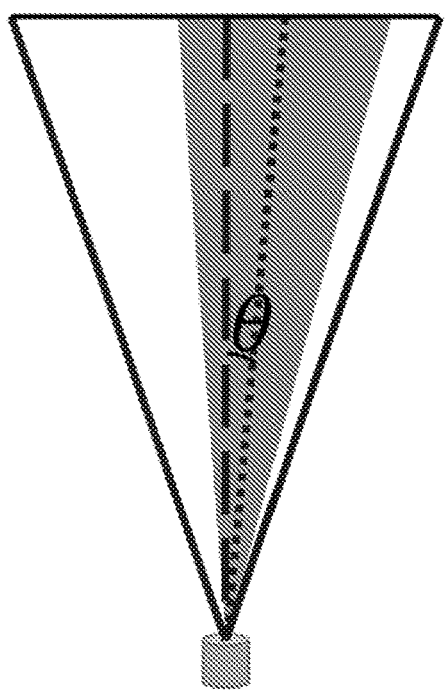

With the OI centered in the detector FoV, the user is then instructed laterally move his head (or his head and body together) in a motion such as shown in FIG. 7B (similar to as in FIG. 2A). As the user moves laterally back and forth, the OI will be visible in camera FoV within an angle θ in the images, shown in FIG. 7C.

Figure 7D:
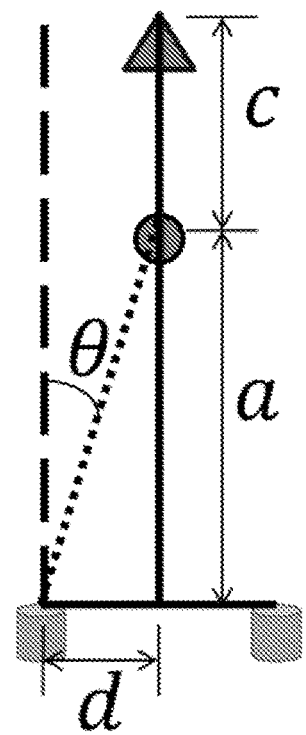

To calculate this angle, the distance to the OI and the distance the head moves are measured in real-time. Referring to FIG. 7D, the distance to the OI, a, is selected before module II and adjusted after the completion of module II, i.e., when the OI is located in the center of the FoV. The amount of head translation from the initial position, d, is tracked using the built-in motion tracking sensors 162 (acceleration and gravity sensors, etc.) after the initiation of stabilization methods described herein. Given the OI distance, a, and the lateral head shift, d, the rotation angle of the principle ray for cropping is $\tan^{-1}(d/a)$ to keep the OI at the center of prosthetic VF. Since the method to extract the depth map using the head translation in module I also uses the head tracking sensors, this method is efficient for such a system. This method also can be implemented by any sort of depth camera system.

Figure 6:
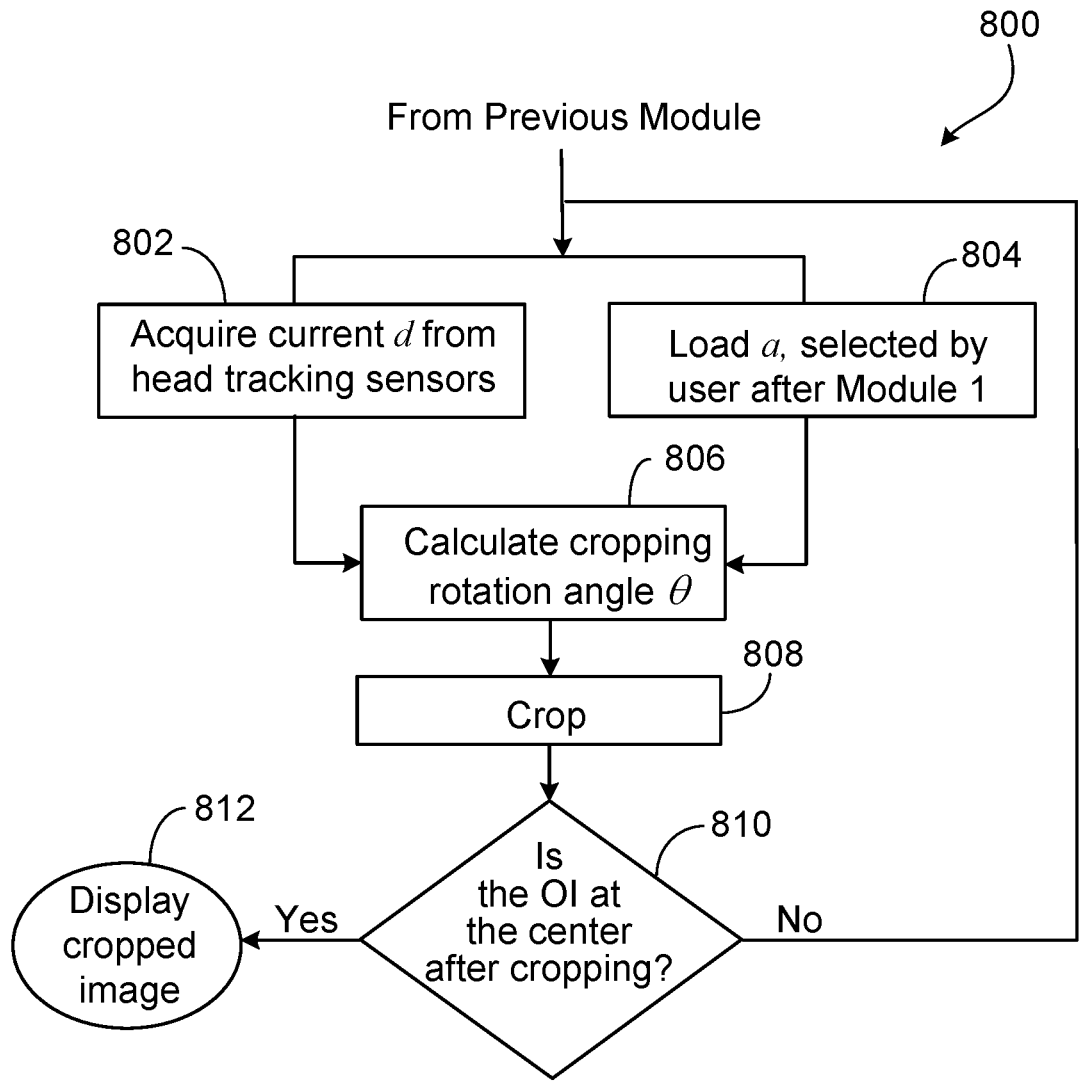
FIG. 6 is a flow chart showing a series of sub-steps for delivering information about a user's environment to the user using an imaging system.

The method used is shown in a flowchart 800 of FIG. 6. In step 510 shown in FIG. 4, the OI has been detected at the center of the camera FoV and the system 100 moves to the first step of module III, where the processor 106 receives the amount of head translation from its initial position, d, and the distance to the OI, a, based on the planar distance chosen by the user (steps 802 and 804). The processor 106 then calculates the cropping rotation angle θ at step 806 using the equation above and crops the image so that the OI is centered in the prosthetic VF, at step 808. In some implementations, the processor 106 will crop the angle θ plus or minus a small additional angle. The processor 106 then confirms that the OI is positioned at or near the center of the cropped image at step 810. If not, the system returns to steps 802 and 804 to try again. If yes, the processor 106 determines that the image has been successfully cropped with a centered OI. Next, at step 812, signals can be transmitted to the visual prosthesis 160 worn by the user or embedded within the user's eye. The representative images generated in step 808 can be converted to electrical signals that are compatible with retinal implants or other types of visual prostheses, and the electrical signals can be delivered to the prosthesis 160 (e.g., via signal transmitter 108). Similar signals can also be delivered to other sensory organs serving the prosthesis such as the skin and/or the tongue, for example. The visual prosthesis can have electrodes configured to provide binary signals or bipolar multi-level signals (e.g., three levels, four levels, or more).

The advantage of the methods described herein are illustrated in FIGS. 8A-9E, which illustrate the differences in object presentation using this stabilization system of the OI at the center of the VF vs. conventional system. FIG. 8A shows three different side-by-side head positions a user might take while looking at the circle OI, left, middle, and right, with the middle position placing the OI along the viewer's principal ray when the viewer is staring into the distance. As illustrated in FIG. 8C, at this position the OI is at the center of both the FoV of the image detector (above)

and the center of the prosthetic VF (below). However, with a narrower VF for the visual prosthesis compared to FoV of the detector, a natural head movement can easily move the OI out of the narrow VF of the prosthesis, either a motion to the left (FIG. 8B) or to the right (FIG. 8D). An example left to right motion is also depicted in FIG. 8E, with OI 902 moving from the right edge to the left edge of the prosthetic VF at positions corresponding to numbers 1-5 in FIG. 9A, making examination of the object difficult.

A preferable scenario is when the OI is stabilized at the center of the prosthetic VF, which might be achieved by training head movements with both translations and deliberate rotations simultaneously. However, to decide the amount of rotation can be difficult without distinctive inputs. Therefore, the system assists the stabilization of the OI at the center of the prosthetic VF. FIGS. 9A-9E show simulated prosthetic images using the disclosed methods to crop the OI from the camera images to display the OI at the center of the prosthetic VF, mimicking this natural head movement with eye rotations for object examination strategy. FIG. 9A shows three different side-by-side head positions a user might take while looking at the circle OI, left, middle, and right. The middle position places the OI along the viewer's principal ray if the viewer is gazing straight ahead.

Although the principal ray of the camera (represented by the dashed lines in FIG. 9A) does not rotate as does the eye during a viewer's natural head movements (as shown in FIG. 8A), cropping camera images can simulate the effect of eye rotation. Using rotated principal rays (the dotted lines in FIG. 9A), the OI can be cropped and shown at the center of the prosthetic VF regardless of the head movement, where a motion of the detector (and/or head of the user) to the left (FIG. 9B) or to the right (FIG. 9D) allows the OI to remain in the center of the cropped final image, as if the OI were in fact on the principal ray (as in FIG. 9C). An example left to right motion is depicted in FIG. 9E using these methods, with OI 1002 remaining largely in the center of the cropped image although the FoV of the detector moves from left to right. The user's head movements with the cropping provides motion parallax cues similar to the vestibular-ocular reflex in human vision enabling the users to visually separate the OI (stabilized at the center of the VF) from background clutter (moving across the VF), and thus assisting object recognition.

In some implementations, once the user has examined the selected OI, the next OI can then be processed. For example, the system 100 can return to step 404 in FIG. 3, and the user can select another plane of interest that includes another potential OI, and proceed through the remaining steps once again. In other implementations, at step 404 the user can select the same plane of interest selected previously. This could be useful if there are multiple (e.g., two or more) potential OIs within the same depth plane. The system 100 could eliminate or otherwise mark the OI as already examined, and proceed to the next OI in the same plane.

Feature Matching

Another method that can be used for cropping is feature matching. The processor 106 first matches distinctive features in the selected OI in camera images across multiple views (e.g., as in FIG. 7B). In this instance, rather than calculating an angle that includes the OI, the OI is directly detected and cropped from the camera images based on its distinctive features. The cropped image (containing the OI and optionally some of the background surrounding the OD is presented to show the user 152 in the prosthesis 160. As in this approach the area for cropping is directly selected from the features in image information, there is no need to track the head translation, and the system can be simplified by not including motion sensors 162 but simply the detector 102 or other depth detector.

Hardware and Software Implementations

The systems disclosed herein can serve as a front-end imaging system for any of a variety of retinal or cortical implants, visual prostheses, and sensory substitution devices (SSDs), and with minimal adjustment or tuning, substantially improving the user's object recognition performance. Compared with systems that do not implement the proposed methods disclosed herein, the systems disclosed herein reduce interpretation times significantly and at the same time, permit more active exploration of the user's environment.

Typically, the imaging system 100 is worn or carried by the user to enable navigation within, and interaction with, the user's environment. In some embodiments, the system 100 is configured to be wearable, and is partially or fully integrated into one or more articles of clothing or other wearable apparatus.

In certain embodiments, the imaging system 100 is implemented as a head-mounted apparatus such as sunglasses, eyeglass frames, or a hat. In certain embodiments, the control unit 104 can be worn on another part of the user's body (e.g., at the waist) and is connected to the detector 102 via a wired or wireless connection. In addition, the system can be added on accessories such as, for example, a cane, a ring, a bracelet, a necklace, a pin, a pendant, and/or gloves.

Figure 10A:
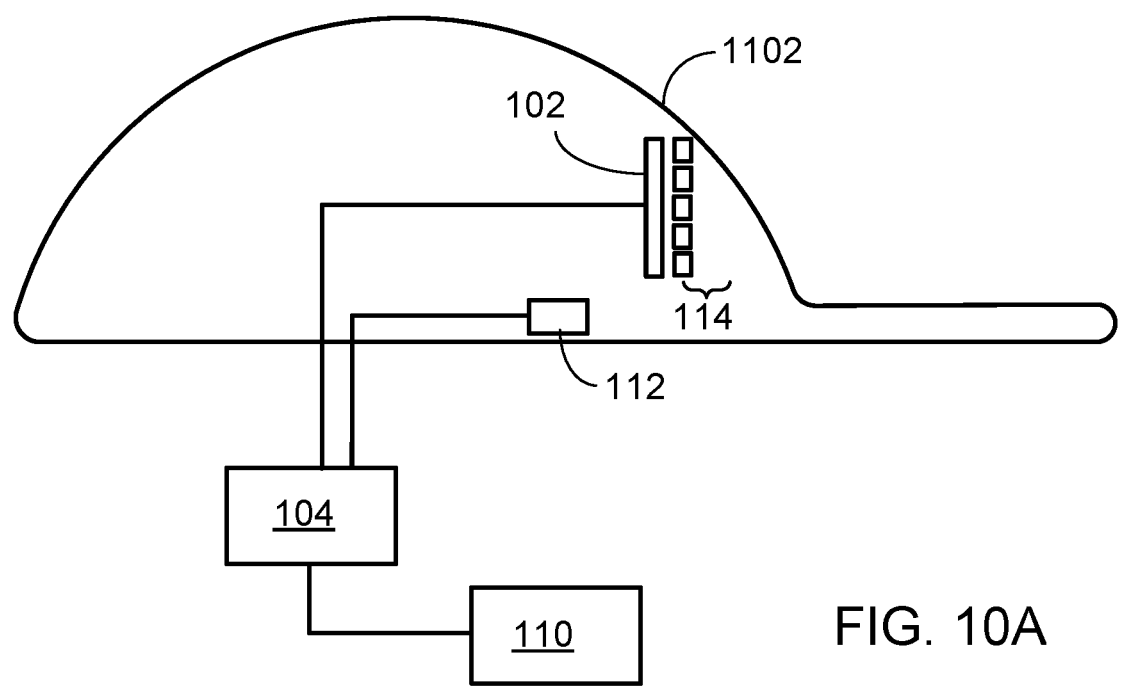
FIGS. 10A and 10B are schematic diagrams showing imaging systems at least partially integrated into a hat and eyeglass frames, respectively.

In certain embodiments, the imaging system 100 is implemented as a head-mounted apparatus. FIG. 10A shows one embodiment of a head-mounted apparatus in which certain components of system 100 are integrated into a hat 1102 worn by the user. In particular, the depth sensors (lens array, IR sensor array, camera array, etc.) 114 and the detector 102 are positioned in a front portion of the hat 1102, while the output device 112 is positioned in a lateral portion of the hat 1102. In some embodiments, the control unit 104 can be positioned within the hat 1102 as well, and connected to the detector 102 to provide operating power for the detector. In certain embodiments, as shown in FIG. 10A, the control unit 104 can be worn on another part of the user's body (e.g., at the waist) and is connected to the detector 102 via a wired or wireless connection. In addition, the system can be added on accessories such as, for example, a cane, a ring, a bracelet, a necklace, a pin, a pendant, and/or gloves.

The input interface 110 can be connected directly to the control unit 104 and worn in a location proximate to the control unit 104 to allow the user to send instructions and issue commands to the control unit 104. In certain embodiments, the input interface 110 can be positioned on another article (e.g., integrated into the handle of a long cane) and can be connected to the control unit 104 via a wired or wireless connection.

Figure 10B:
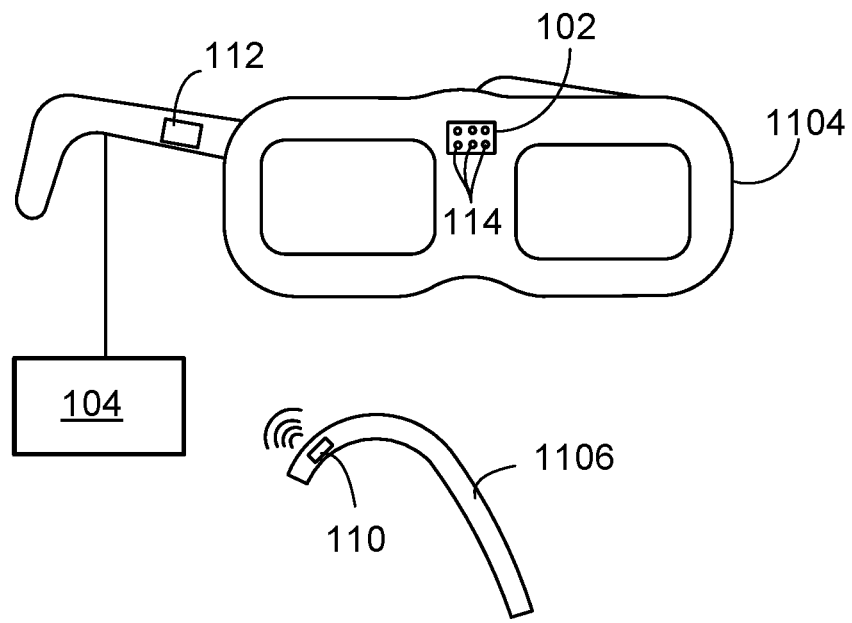

In another head-mounted implementation, the depth sensors (lens array, IR sensor array, etc.) 114, the detector 102, and the output device 112 are integrated into eyeglass frame as shown in the schematic view of FIG. 10B. The detector 102 and the output device 112 are connected to the control unit 104 through the eyeglass frames 1104, and the control unit 104 is configured to worn at the waist of the user as described above. The input interface 110 is integrated into the handle of a cane 1106, and is wirelessly connected to the control unit 104. The detector 102 and the output device 112 are connected to the control unit 104 through the eyeglass frames, and the control unit 104 is configured to worn at the waist of the user as described above. The input interface 110 is integrated into the handle of the cane 1106, and is wirelessly connected to the control unit 104.

The steps described herein can be implemented in computer programs using standard programming techniques. Such programs are designed to execute on programmable computers or specifically designed integrated circuits, each including an electronic processor (e.g., the processor 106), a data storage system (including memory and/or storage elements), at least one input device, and least one output device, such as an electrode array, display or tactile array. The program code is applied to input data (e.g., depth information and image information) to perform the functions described herein and generate output signals and/or information. Each such computer program can be implemented in a high-level procedural or object-oriented programming language, or an assembly or machine language. Furthermore, the language can be a compiled or interpreted language. Each such computer program can be stored on a tangible, physical computer readable storage medium (e.g., ROM, USB memory) that when read by a computer or electronic circuit can cause the processor in the computer or circuit to perform the analysis and control functions described herein.

EXAMPLES

Certain aspects are further described in the following examples, which do not limit the scope of the claims.

Example 1—Impact of Guided Cropping Using Motion Parallax on Object Recognition The present example shows the impact of guided cropping using motion parallax for background de-cluttering with motion parallax on object recognition.

Figure 11A:
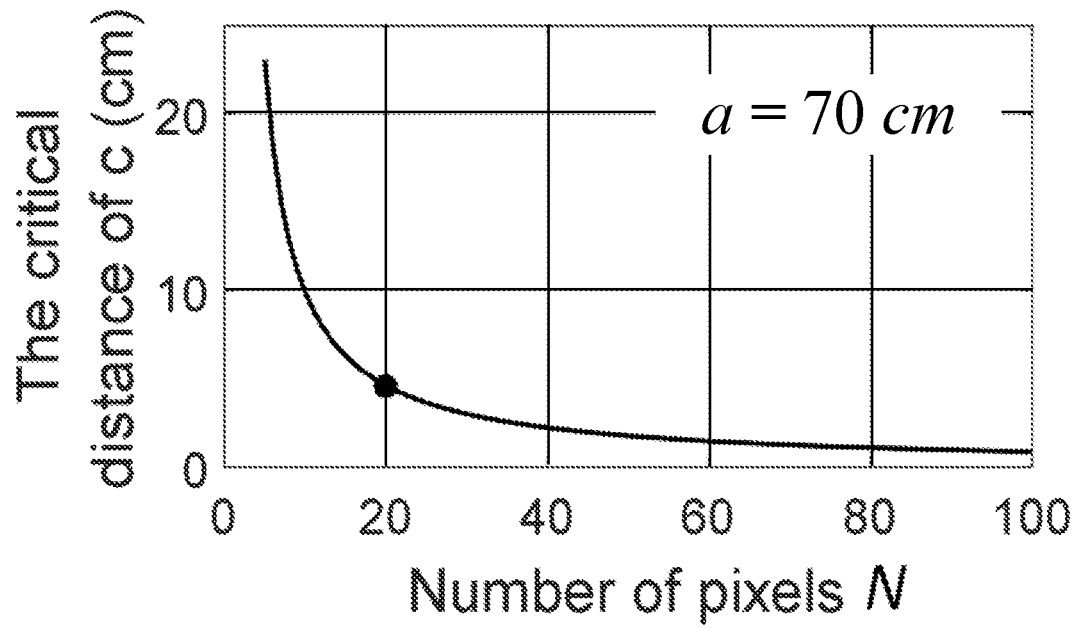
FIGS. 11A and 11B are graphs showing the effect of pixel count and distance between an observer and an object of interest on the critical distance between an object of interest and background.
Figure 11B:
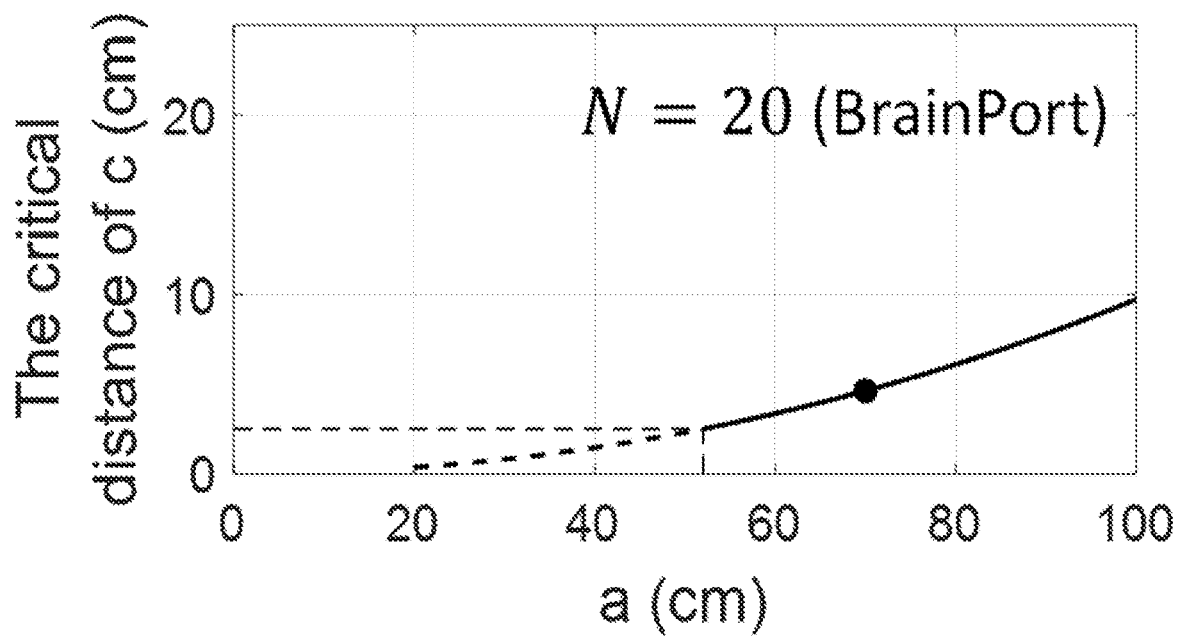

To understand the capacity of the proposed system better, the system's performance was simulated using MatLab® under practical scenarios and mostly according to the parameters achieved by the BrainPort® device (as an example). Referring again to FIG. 7D, the distance to the OI is "a", the amount of head translation from the initial position is "d", and the distance from the OI to the background is "c". For the graphs shown in FIGS. 11A and 11B, d=12 cm, camera FoV=50°, prosthetic VF=24°. FIG. 11A shows that the critical distance of c (the minimum distance that the background would shift at least 1 pixel to see the motion) decreases with an increasing number of pixels N. For a number of pixels N=20, FIG. 11B illustrates that critical distance of c increases with distance a. Thus, the higher number of pixels N, the better the separation, and the closer a, the better the separation, which allows for optimization of the techniques described herein. The critical distance of c can thus be controlled and optimized by adjusting the number of pixels N of the prosthetic device used.

Example 2—Simulations of Stabilization of OIs

To illustrate the effects provided by the proposed system, an image database was created that simulated the stabilization of the OI at the center of prosthetic views. Object recognition was tested in normally sighted subjects using these simulated images.

Image Database with Simulated Stabilization of the OI at the Center of Prosthetic Views The BrainPort® V200 (with a prosthetic resolution of 20×20 pixels) together with the proposed system described herein were shown to accurately control the translation and rotation amount. Images were acquired through the BrainPort® web application that displays the camera views and simulated 20×20 pixels prosthetic views with 256 grey levels.

The grayscale image database includes 35 familiar objects (e.g., a teapot, headphones, and sneakers) placed in front of synthetic background images at 6 complexity levels and photographed from 9 lateral viewpoints. Schematic Dead Leaves images mimicking natural image statistics were used as background images allowing systematic control of complexity. The objects were placed within arm's reach distances (30 cm, 50 cm, or 70 cm) and the background images were located 115 cm from the BrainPort® camera. The range of viewpoints lateral shift was 24 cm, and the 9 viewpoints were 3 cm apart. The rotation angle at each viewpoint for each object was calculated to maintain the object in the center of camera FoV. A total of 1890 simulated images were acquired.

Performance of Object Recognition with the Simulated Images

To see the impact of the proposed method, object recognition was tested in normally sighted subjects using these simulated prosthetic images presented with HMD. The motion sensors in HMD tracked the subjects' lateral head positions and showed the corresponding pre-captured images. Six experimental conditions (2×3) were tested: background (with or without clutter)×object viewing conditions (static single viewpoint, 9 coherent viewpoints corresponding to subjects' head positions, and 9 randomly presented viewpoints). The object was centered in all images as simulation of the proposed stabilization of the OI.

Figure 12:
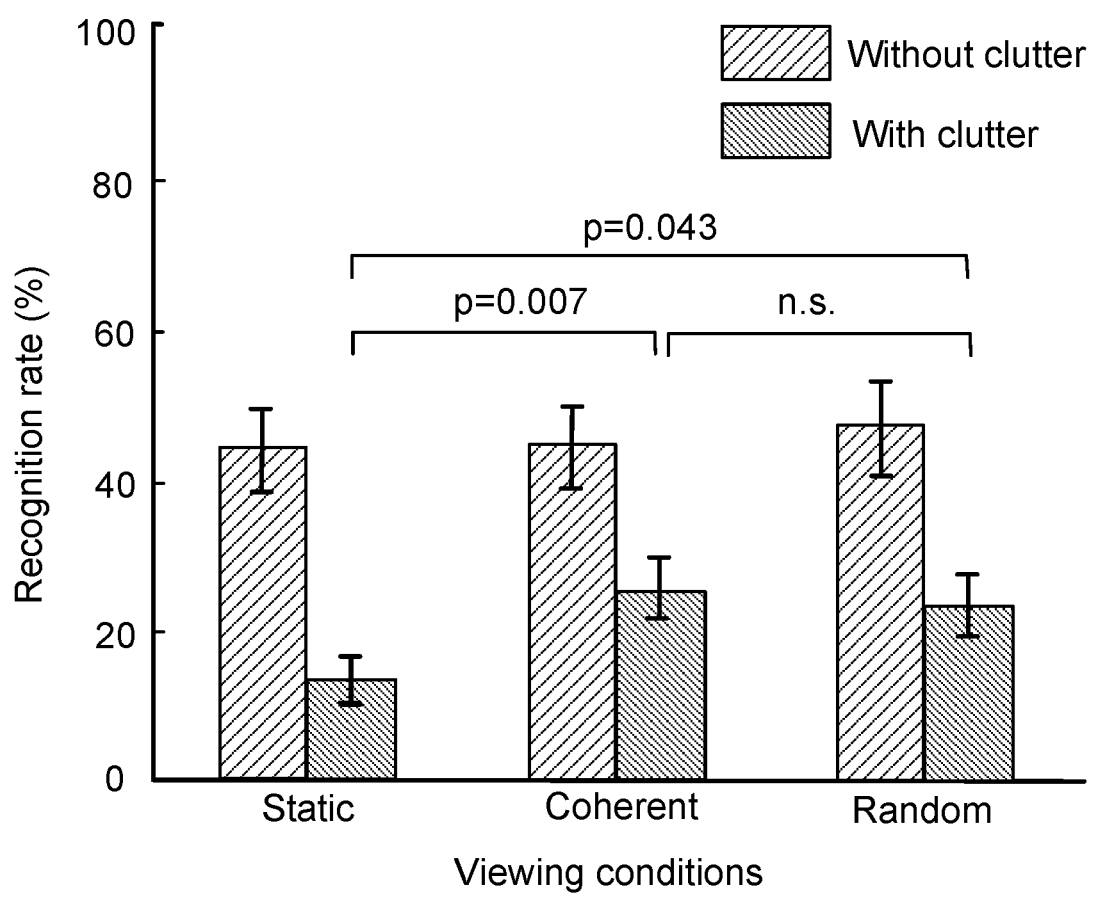
FIG. 12 is a graph showing recognition rates by users in various viewing conditions.

As shown in FIG. 12, without background clutter, average recognition rate was about 45% for all viewing conditions. Performance with clutter dropped to 14% in the static condition, but was significantly improved in both motion parallax conditions: 26% for coherent viewpoints and 24% for random viewpoints. The motion parallax cues from the stabilization of the OI at the center of prosthetic VF improved object recognition in a cluttered environment, and the improvement did not require coherent viewpoints.

Other Embodiments

A number of embodiments have been described. Nevertheless, it will be understood that various modifications may be made without departing from the spirit and scope of the disclosure. For example, the imaging system 100 described herein is particularly well suited to provide information to a vision-impaired user; however, the imaging system 100 also can be used to provide information in a variety of applications where a reduced-resolution representation of the user's environment is useful, e.g., when the "user" is a robot or autonomous air-borne or water-borne drone, or surveillance system, in an auto-tracking system. These applications include environments with low-lighting and poor visual conditions (e.g., total darkness, dense fog, underwater, or smoke conditions). Although a single camera has been described, the lateral head motion described in this disclosure can be replaced with a series of cameras that are positioned in a lateral sequence or moving camera on the rail system. Rather than requiring the user to move their head back and forth (as described for Module III) the system 100 can use the known, fixed distance between cameras to provide distance d. Accordingly, other embodiments are within the scope of the following claims.

What is claimed is:

1. A system for providing information about an environment to a user within the environment, the system comprising:
   a detection apparatus configured to obtain depth and image information about the environment, wherein the depth and image information comprises data relating to potential objects of interest at multiple distances relative to a position of the user within the environment; and
   an electronic processor in communication with the detection apparatus, wherein the electronic processor is configured to:
      obtain, from the depth and image information, a set of one or more depth planes containing the potential objects of interest;
      receive input comprising a user selection of an object of interest from among the potential objects of interest;
      provide output to guide the user to move the detection apparatus to position the object of interest near a reference point on a field of view of the detection apparatus;
      obtain multiple images of the object of interest during the user's movement of the detection apparatus; and
      generate cropped images from the multiple images such that the object of interest is kept near a reference point on each of the cropped images and such that the reference point on at least one of the cropped images is offset from the reference point on the field of view.

2. The system of claim 1, further comprising motion sensors configured to measure motions and displacements of the detection apparatus.

3. The system of claim 2, wherein:
   the motion sensors are configured to measure an initial position of a head of the user when the user selects the object of interest,
   the electronic processor is configured to provide output to guide a lateral shift of a head of the user to adjust a position of the field of view, and
   the motion sensors are configured to measure a distance of the lateral shift relative to the initial position of the head.

4. The system of claim 1, wherein the electronic processor is configured to adjust a position of the field of view by a distance substantially matching a distance of a lateral shift of a head of the user.

5. The system of claim 4, wherein:
   the electronic processor is configured to calculate:
      a principal rotation angle of a principal ray for the object of interest from the head after the lateral shift, and
      a distance of the object of interest from the detection apparatus, and the electronic processor is configured to generate the cropped images based on the principal rotation angle and present each of the cropped images to the user.

6. The system of claim 1, wherein the reference point on each of the cropped images is a center of each of the cropped images, and the electronic processor is configured to:
   identify portions of the multiple images that correspond to the object of interest by identifying a feature of the object of interest, and
   generate the cropped images such that the object of interest is near the center of the each of the cropped images,
   wherein the electronic processor is configured to present each of the cropped images to the user.

7. The system of claim 1, wherein the detection apparatus comprises a depth camera system comprising one or more of a light-field camera, stereo camera, IR-based depth camera, or a multiple camera array.

8. The system of claim 1, wherein the depth and image information comprises a set of depth sliced images each corresponding to a depth plane at a different distance relative to the position of the user, wherein the depth sliced images comprise confocal images.

9. The system of claim 1, wherein the one or more depth planes are positioned at one or more distances relative to the position of the user within the environment, the one or more distances being within a range bounded by a minimum distance value.

10. The system of claim 1, wherein the one or more depth planes are positioned at one or more distances relative to the position of the user within the environment, the one or more distances being within a range bounded by a maximum distance value.

11. The system of claim 1, wherein the electronic processor is configured to obtain the one or more depth planes by determining an operating mode associated with the system.

12. The system of claim 1, wherein the electronic processor is further configured to convert the cropped images into electrical signals, and to transmit the electrical signals to a visual prosthesis worn by the user.

13. The system of claim 1, further comprising an input interface configured to receive input information from the user and to transmit the input to the electronic processor based on the input information.

14. The system of claim 13, wherein the input interface comprises a controller mounted to a cane, or a voice-activated interface.

15. The system of claim 1, wherein the electronic processor is configured to track the object of interest in a depth plane.

16. The system of claim 1, wherein the reference point on the field of view is a center of the field of view, and the reference point on each of the cropped images is a center of each of the cropped images.

17. A method of providing information about an environment to a user within the environment, the method comprising:
   obtaining, using a detection apparatus, depth and image information about the environment, wherein the depth and image information comprises data relating to potential objects of interest at multiple distances relative to a position of the user within the environment;
   obtaining, from the depth and image information, a set of one or more depth planes containing the potential objects of interest to the user;
   receiving input comprising a user selection of an object of interest from among the potential objects of interest;
   providing output to guide the user to move the detection apparatus to position the object of interest near a center of a field of view of the detection apparatus;
   obtaining multiple images of the object of interest during the user's movement of the detection apparatus; and
   generating cropped images from the multiple images such that the object of interest is kept near a center of each of the cropped images and such that the center of at least one of the cropped images is offset from the center on the field of view.

18. The method of claim 17, further comprising detecting motions and displacements of the detection apparatus.

19. The method of claim 17, further comprising:
providing an output to guide a lateral shift of a head of the user to adjust a position of the field of view; and
measuring a distance of the lateral shift of the head relative to an initial position of the head.

20. The method of claim 17, further comprising adjusting a position of the field of view by a distance substantially matching a distance of a lateral shift of a head of the user.

21. The method of claim 20, further comprising calculating an angle representing a principal rotation angle of a principal ray for the object of interest from the head after the lateral shift,
wherein generating the cropped images comprises:
generating the cropped images based on the principal rotation angle of the principal ray, and
presenting each of the cropped images to the user.

22. The method of claim 17, further comprising:
identifying portions of the multiple images that correspond to the object of interest by identifying a feature of the object of interest; and
presenting each of the cropped images to the user.

23. The method of claim 17, further comprising:
converting the cropped images into electrical signals, and transmitting the electrical signals to a visual prosthesis worn by the user.

* * * * *